United States Patent [19]

Fruhwald

[11] Patent Number: 4,642,172
[45] Date of Patent: Feb. 10, 1987

[54] CONTROLLED-POTENTIAL BIAS CIRCUIT FOR ELECTROCHEMICAL CELLS

[75] Inventor: John M. Fruhwald, Pittsburgh, Pa.

[73] Assignee: Bacharach, Inc., Pittsburgh, Pa.

[21] Appl. No.: 703,168

[22] Filed: Feb. 19, 1985

[51] Int. Cl.[4] .................. C25B 15/00; G01N 27/46
[52] U.S. Cl. .................. 204/231; 204/406; 204/412; 204/432
[58] Field of Search .............. 204/228, 231, 406, 412, 204/432

[56] References Cited

U.S. PATENT DOCUMENTS

| | | | |
|---|---|---|---|
| 3,909,386 | 9/1975 | Oswin et al. | 204/195 |
| 3,944,473 | 3/1976 | Spaepen et al. | 204/228 |
| 4,123,700 | 10/1978 | LaConti et al. | 324/29 |
| 4,227,988 | 10/1980 | Galwey et al. | 204/231 |
| 4,348,632 | 9/1982 | Galwey et al. | 204/231 X |

Primary Examiner—Donald R. Valentine
Attorney, Agent, or Firm—Webb, Burden, Robinson & Webb

[57] ABSTRACT

A bias circuit (13) for an electrochemical fuel cell (15) serving for example as a carbon monoxide or hydrogen sulfide detector, including an operational amplifier tied to the anode and reference terminals (21,23) of the fuel cell (15), and a zener diode (50) arrangement for maintaining a predetermined voltage drop between the output and negative inputs of the operational amplifier (33).

7 Claims, 1 Drawing Figure

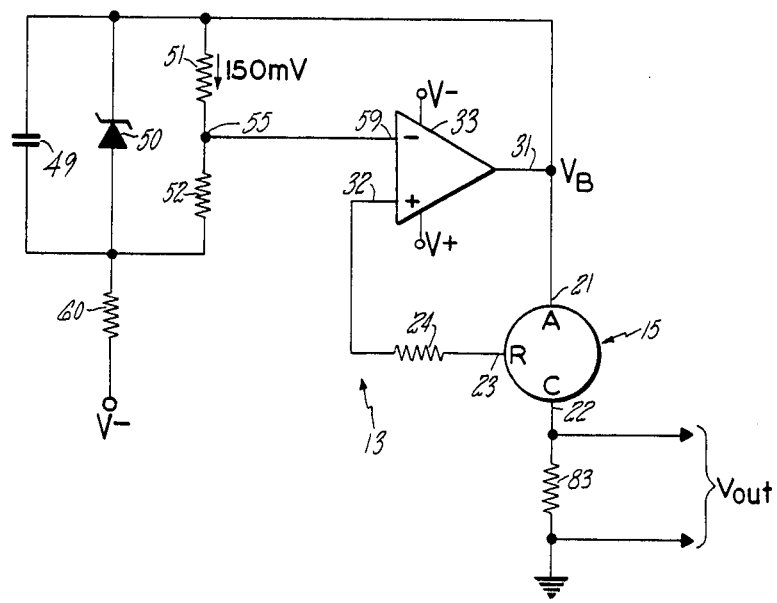

CONTROLLED-POTENTIAL BIAS CIRCUIT FOR ELECTROCHEMICAL CELLS

DESCRIPTION

1. Technical Field

The technical field pertinent hereto relates to electrochemical cells, and more particularly bias circuits for electrochemical cells used as carbon monoxide or hydrogen sulfide detectors.

2. Background Art

In prior bias circuits for electrochemical cells in particular those used as carbon monoxide or hydrogen sulfide detectors, two power supplies and one or more operational amplifiers have been required for effective operation.

In particular, a negative power supply is required in such circuits of the prior art to bias the reference terminal of the electrochemical cell, and a positive power supply is required oppositely to bias the anode of the electrochemical cell. This effectively biases the reference terminal 150 mV, for example, lower than the anode, as required.

Unfortunately, each operational amplifier used inherently introduces substantial error during operation because of its offset voltage and its bias current.

Further background regarding presently utilized biasing circuits related to the same technical field is found in "Controlled-Potential Electrochemical Analysis of Carbon Monoxide," by K. F. Blurton and H. W. Bay, in the publication *American Laboratory* (July 1974). By way of additional background, General Electric Company has developed a circuit relevant as background herein, under Contract Number HO357078, Dec. 19, 1975, for the United States Department of the Interior, Bureau of Mines.

SUMMARY OF THE INVENTION

According to the invention herein, the anode potential of an electochemical cell used as a gas detector or sensor is boosted or controlled by the output of an operational amplifier (rather than the voltage level of the cathode thereof being pulled down or otherwise influenced) in order to establish the potential of the reference connection at a selected relative level with respect to the anode.

In particular, voltage setting means such as a voltage divider including a connecting node, in parallel with a low-voltage diode for example establishes the selected voltage difference or bias level between the reference and anode connections of the sensor.

According to one version of the invention, the operational amplifier has a negative input which is driven by the connecting node of the voltage divider to maintain the selected bias level between the anode and reference electrodes of the electrochemical cell.

Accordingly, the arrangement of the invention establishes a predetermined voltage difference between the sensor's anode and reference terminals, as required for effective biasing operation.

According to the invention, the voltage level of the anode connection of the electrochemical cell is controlled with respect to the reference connection thereof and thus floats with respect to the voltage level of the power supply, thereby permitting the current through the sensor's cathode to be referenced to a selected common potential.

BRIEF DESCRIPTION OF THE DRAWING

The FIGURE is a schematic illustration of a bias circuit for an electrochemical sensor, according to the invention herein.

DETAILED DESCRIPTION OF A BEST MODE FOR CARRYING OUT THE INVENTION

The FIGURE shows a biasing circuit 13 for an electrochemical cell or sensor 15 including anode, cathode and reference terminals, respectively 21, 22, and 23.

The anode and reference terminals of sensor 15 are respectively electrically connected to the output 31 and positive input 32 of an operational amplifier 33.

A voltage setting means including for example a zener diode 50 or a well-known bandgap reference circuit is connected electrically in parallel with first and second resistors, respectively 51 and 52. The resistors 51, 52 are in turn connected at a connecting node 55 to comprise a voltage divider. The node 55 leads to the negative input 59 of operational amplifier 33.

Operational amplifier 33 is preferably an Intersil 7642 CMOS device. Resistors 51 and 52 are respectively rated at 14K and 100K ohms. The zener diode 50 is for example an Intersil 8069 device according to a preferred version of the invention. Other values of resistor 51 and 52 can be employed to produce a variety of selected bias voltages ranging for example between 50 and 150 millivolts, or other bounds depending upon the detector hardware selected.

Further, the zener diode 50 is shunted by a parallel capacitor 49 (about 4.7 microfarad for example) to stabilize the active elements in that portion of the biasing circuit 13.

By way of further detail, the cathode of zener diode 50 is connected to the output 31 of operational amplifier 33. An additional resistor 60 is connected at one end to a selected negative voltage level (V-) derived from the battery voltage employed and to the anode of zener diode 50 at the other end. This resistor 60 is preferably at 27K ohms and assists in fixing the precise voltage drop across diode 50.

In this manner, according to a preferred version of the invention, the reference node 23 of the electrochemical cell 15 is maintained at a fixed bias level of about $-150$ mV for example with respect to the anode 21 thereof. The anode 21 is thus independent of the voltage drop across resistor 83, which varies with the presence of the gas being detected by the electrochemical cell 15. Therefore, the current through sensor 15 is referenced to a selected common potential.

In particular, this common potential can be generated by a commercially available voltage regulator or voltmeter chip, such as for example an Intersil 7136 device which requires only a single power supply such as a 9 volt transistor radio battery. The voltage difference between the anode and reference terminals is thus made independent of the current level generated between the anode and cathode terminals, 21 and 22 respectively, by the presence or absence of the gas to be detected by the sensor.

The connection between the positive input 32 to operational amplifier 33 and reference node 23 may include a low current protective resistor 24 rated at 10K for example. This protects amplifier 33 from static discharge with respect to operational amplifier input 32.

Further, the cathode of electrochemical cell 15 is connected to common potential through a selected output load resistor 83 straddled by output terminals for a desired output voltage level $V_{OUT}$.

The biasing circuit 13 including operational amplifier 33 thus in effect lifts the level of the sensor anode 21 until the reference level 23 is controlled at for example 150 mV below the operational amplifier output 31. This 150 mV difference is produced by the indicated connection of resistors 51 and 52 in parallel with zener diode 50.

Individuals skilled in the art are likely to conceive of additional versions of the invention after reading the description above. Accordingly, attention to the claims which follow is urged, as these define the metes and bounds of the invention with particularity.

I claim:

1. A bias circuit for an electrochemical cell including anode, cathode and reference terminals, said bias circuit comprising an amplifier having an output electrically connected to the anode of the cell, a positive input connected to the reference terminal, and a negative input; and voltage setting means connected to the negative input of the amplifier for establishing a predetermined voltage difference, said voltage setting means being effective for establishing a voltage drop defined by the voltage difference between said output and said negative input of said amplifier, whereby the predetermined voltage difference is independent of the current variation between the anode and cathode terminals of the electochemical cell.

2. The bias circuit of claim 1, wherein said voltage setting means includes a zener diode.

3. The bias circuit of claim 2, wherein said zener diode is shunted by a stabilizing capacitance.

4. The bias circuit of claim 1, wherein the electrical connection between said positive input of the amplifier and the reference terminal of the electrochemical cell is accomplished through a protective resistor.

5. The bias circuit of claim 1, wherein said amplifier means is an operational amplifier.

6. The bias circuit of claim 1, wherein said voltage setting means includes a bandgap reference circuit.

7. The bias circuit of claim 6, wherein said bandgap reference circuit is shunted by a stabilizing capacitance.

* * * * *